(12) United States Patent
Shibata

(10) Patent No.: US 11,383,014 B2
(45) Date of Patent: Jul. 12, 2022

(54) BLOOD PURIFYING DEVICE AND ACCESS FLOW RATE MEASURING METHOD

(71) Applicants: Artisan Lab Co., Ltd., Tokyo (JP); NIPRO CORPORATION, Osaka (JP)

(72) Inventor: Kazuhiko Shibata, Tokyo (JP)

(73) Assignees: ARTISAN LAB CO., LTD, Tokyo (JP); NIPRO CORPORATION, Osaka (JP)

(*) Notice: Subject to any disclaimer, the term of this patent is extended or adjusted under 35 U.S.C. 154(b) by 767 days.

(21) Appl. No.: 16/131,104

(22) Filed: Sep. 14, 2018

(65) Prior Publication Data

US 2019/0076594 A1    Mar. 14, 2019

(30) Foreign Application Priority Data

Sep. 14, 2017 (JP) .............................. JP2017-176964

(51) Int. Cl.
*A61M 1/36* (2006.01)
*A61M 1/16* (2006.01)

(52) U.S. Cl.
CPC .......... *A61M 1/3658* (2014.02); *A61M 1/361* (2014.02); *A61M 1/3644* (2014.02);
(Continued)

(58) Field of Classification Search
CPC .. A61M 1/1605; A61M 1/361; A61M 1/3644; A61M 1/3649; A61M 1/3656;
(Continued)

(56) References Cited

U.S. PATENT DOCUMENTS 5,685,989 A * 11/1997 Krivitski ............. A61M 1/3658
                                                    210/103
6,189,388 B1 * 2/2001 Cole ................... A61M 1/3655
                                                    73/861.07
(Continued)

FOREIGN PATENT DOCUMENTS

JP      10-505766      6/1998
JP      2015-150366    8/2015
(Continued)

OTHER PUBLICATIONS

Kenneth Hoyt, PhD. et al., "Accuracy of Volumetric Flow Rate Measurements: An In Vitro Study Using Modern Ultrasound Scanners", Journal of Ultrasound in Medicine, vol. 28, Issue 11, pp. 1511-1518, Nov. 2009.

(Continued)

*Primary Examiner* — Benjamin J Klein
(74) *Attorney, Agent, or Firm* — Xsensus LLP

(57) ABSTRACT

An object is to provide a blood purifying device and an access flow rate measuring method enabling easy and accurate measurement of an access flow rate of an access vessel. A blood purifying device includes a flow rate calculating unit calculating the access flow rate of an access vessel based on an initial blood indicator for blood distributed through a vein side circuit and flowing through the access vessel of a patient, the flow rate distributed through measuring means when a pump is reversed to cause the priming solution to flow out from an artery side circuit, and a blood indicator for the blood diluted with the priming solution which is obtained when the pump is reversed to dilute, with the priming solution, the blood distributed through the vein side circuit.

12 Claims, 4 Drawing Sheets

(52) U.S. Cl.
CPC ........ *A61M 1/3656* (2014.02); *A61M 1/3663* (2013.01); *A61M 1/1605* (2014.02); *A61M 1/367* (2013.01); *A61M 1/3649* (2014.02); *A61M 1/3669* (2013.01)

(58) Field of Classification Search
CPC .............. A61M 1/3658; A61M 1/3663; A61M 1/3669; A61M 1/367
See application file for complete search history.

(56) References Cited

U.S. PATENT DOCUMENTS

| | | | | |
|---|---|---|---|---|
| 7,590,437 | B2* | 9/2009 | Rubinstein | A61B 5/029 600/317 |
| 7,704,213 | B2* | 4/2010 | Kraemer | A61M 1/3663 604/6.09 |
| 2005/0082226 | A1* | 4/2005 | Bene | A61M 1/16 210/96.2 |
| 2018/0318486 | A1* | 11/2018 | Crnkovich | A61M 1/1601 |

FOREIGN PATENT DOCUMENTS

| | | |
|---|---|---|
| JP | 2017-012648 | 1/2017 |
| JP | 2017-023237 | 2/2017 |
| WO | 96/08305 | 3/1996 |

OTHER PUBLICATIONS

Kazuhiko Shibata et al., "New Method of Measuring Volume of Vascular Access Flow That Requires No Special Device", Nephrology Dialysis Transplantation, vol. 32, Issue suppl_3, pp. iii663, https://doi.org/10.1093 /ndt/gfx178, May 1, 2017.

* cited by examiner

BLOOD PURIFYING DEVICE AND ACCESS FLOW RATE MEASURING METHOD

TECHNICAL FIELD

The present invention relates to a blood purifying device and an access flow rate measuring method using the blood purifying device.

BACKGROUND ART

In hemodialysis, in general, blood is taken from a patient's body at a rate of approximately 100 mL to 300 mL per minute (blood removal) and circulated through a dialyzer for purification, and the purified blood is returned to the patient (retransfusion). To obtain such a flow rate of blood, for example, an artery and a vein are surgically anastomosed to form a vessel (access vessel) referred to as a shunt. During hemodialysis, the blood is removed through the access vessel for dialysis. A high flow rate of access blood imposes an extra burden on the heart, leading to the risk of a heart failure, and a low flow rate of access blood precludes sufficient dialysis. Accurately measuring the flow rate (access flow rate) of blood through the access vessel is thus important.

A method using ultrasonic waves, such as a Doppler method, has mainly been used to measure the access flow rate. For example, an artificial dialysis system in PTL 1 is provided with an ultrasonic transmitting and receiving unit (ultrasonic probe) transmitting and receiving ultrasonic waves to and from a part of the vessel between an outlet portion and an inlet portion to ultrasonically measure blood flow velocity. By way of example, the Doppler method is used to calculate the blood flow velocity in the artificial dialysis system. A method has also been prevalent that uses a Doppler-echo method to measure the inner diameter of the vessel and the blood flow velocity to measure the access blood flow. This method has been reported to be accurate to some degree (NPL 1). However, the method involves a measurer's skills and careful operations. Shibata et al. reports that a method of reversely connecting a dialysis circuit to dilute an access blood flow with a priming solution for measurement has a very high correlation with the access blood flow measured by the Doppler-echo method using modern equipment (NPL 2).

CITATION LIST

Patent Literature

[PTL 1] Japanese Translation of PCT International Application, Publication No. H10-505766

Non Patent Literature

[NPL 1] Kenneth Hoyt, PhD. Accuracy of Volumetric Flow Rate Measurements An In Vitro Study Using Modern Ultrasound Scanners. J Ultrasound Med. Author manuscript; available in PMC 2012 Aug. 9. Published in final edited form as: J Ultrasound Med. 2009 November; 28(11): 1511-1518

[NPL 2] Kazuhiko Shibata etc., NEW METHOD OF MEASURING VOLUME OF VASCULAR ACCESS FLOW THAT REQUIRES NO SPECIAL DEVICE Nephrology Dialysis Transplantation, Volume 32, Issue suppl 3, 1 May 2017, Pages iii663

SUMMARY OF INVENTION

Technical Problem

However, measurement of the blood flow rate using the Doppler method as described in PTL 1 is disadvantageously difficult and not so accurate. There has thus been a demand to develop a blood purifying device and an access flow rate measuring method enabling easy and accurate measurement of the access flow rate.

In view of these circumstances, an object of the present invention is to provide a blood purifying device and an access flow rate measuring method enabling easy and accurate measurement of the access flow rate.

Solution to Problem

To accomplish the aforementioned object, the present invention adopts the following solutions.

The present invention provides a blood purifying device including a dialysis unit bringing blood into contact with a dialysate, and a blood circuit having an artery side circuit having an end connected to the dialysis unit and another end to which an artery side puncture needle puncturing an upstream side of an access vessel of a patient is connected and a vein side circuit having an end connected to the dialysis unit and another end to which a vein side puncture needle puncturing a downstream side of the access vessel of the patient is connected, the blood circuit distributing the blood, the artery side circuit being provided with a pump capable of rotating in forward and reverse and circulating the blood, the vein side circuit being provided with a measuring means for measuring a blood indicator for the blood, wherein the blood purifying device includes a flow rate calculating unit calculating an access flow rate of the access vessel based on an initial blood indicator for the blood distributed through the vein side circuit and flowing through the access vessel of the patient, the initial blood indicator being obtained by a system removing the dialysate from the dialysis unit without relying on the pump, a flow rate of blood when the pump is reversed to cause the priming solution to flow out from the artery side circuit, and a blood indicator for the blood diluted with the priming solution when the pump is reversed to dilute, with the priming solution, the blood distributed through the vein side circuit and flowing through the access vessel of the patient.

The blood purifying device according to the present invention includes the pump capable of rotating in forward and reverse. Forward rotation of the pump thus causes blood to be distributed through the blood circuit and dialyzed in the dialysis unit, enabling the blood to be purified. Furthermore, the pump is reversed to cause the priming solution to flow out from the artery side circuit, enabling the blood diluted with the priming solution to be circulated. This allows the blood indicator for the blood diluted with the priming solution (examples of the blood indicator include hemoglobin concentration, hematocrit, urea, albumin, and the like) to be measured using the measuring means. That is, the blood purifying device according to the present invention is capable of measuring the blood indicator for the blood before and after the dilution with the priming solution. Moreover, the blood purifying device according to the present invention includes the flow rate calculating unit calculating the access flow rate of the access vessel based on the flow rate obtained when the pump is reversed and measurement results for the blood indicator for the blood obtained before and after the dilution with the priming solution. This allows the access flow rate to be accurately measured. Furthermore, the blood purifying device according to the present invention is capable of executing both measurement of the access flow rate and hemodialysis. This eliminates a need for replacement of equipment, facilitating measurement of the access flow rate of the access vessel and hemodialysis.

In the blood purifying device, the measuring means is preferably capable of measuring the hemoglobin concentration or hematocrit in the blood.

When the measuring means is capable of measuring the hemoglobin concentration or the hematocrit in the blood, the access flow rate can be measured based on the hemoglobin concentration or the hematocrit in the blood. Furthermore, by the hemoglobin concentration or the hematocrit in the blood being measured before and after the dilution with the priming solution, the access flow rate can be more accurately measured.

Preferably, in the blood purifying device, based on an initial blood indicator BC1 (Blood Concentration 1) for the blood distributed through the vein side circuit and flowing through the access vessel of the patient as a result removal of the dialysate from the dialysis unit with the pump stopped, a flow rate S distributed through the measuring means when the pump is reversed to cause the priming solution to flow out from the artery side circuit, and a blood indicator BC2 (Blood Concentration 2) for the blood diluted with the priming solution which is obtained when the blood indicator for the blood diluted with the priming solution reaches a plateau after the pump is reversed to cause the priming solution to flow out from the artery side circuit to dilute, with the priming solution, the blood distributed through the vein side circuit and flowing through the access vessel of the patient, the flow rate calculating unit calculates the access flow rate (X) of the access vessel based on Equation (1) assuming that the access flow rate in the access vessel is not varied by the priming solution having flowed in from the artery side circuit.

$$X=BC2\times S/(BC1-BC2) \quad (1)$$

The blood purifying device thus uses Equation (1) to calculate the access flow rate based on the flow rate distributed through the measuring means when the pump is reversed and the blood indicator for the blood obtained before and after the dilution with the priming solution. This allows the access flow rate to be accurately and easily measured.

Preferably, in the blood purifying device, the vein side circuit includes a vein side chamber that allows removal of air bubbles in the blood and a vein side liquid level adjusting means for allowing a liquid level in the vein side chamber to be optionally raised and lowered for adjustment, and the vein side liquid level adjusting means adjusts the liquid level in the vein side chamber when a fluid flowing through the vein side circuit is refluxed.

The vein side chamber provided in the vein side circuit allows removal of air bubbles in the blood distributed through the vein side circuit. Furthermore, when the fluid flowing through the vein side circuit is refluxed, the vein side liquid level adjusting means provided in the vein side circuit raises the liquid level in the vein side chamber to allow more reliable prevention of possible mixture of air into the blood.

Preferably, in the blood measuring device, the artery side circuit includes an artery side chamber that allows removal of air bubbles in the blood and an artery side liquid level adjusting means for allowing a liquid level in the artery side chamber to be optionally raised and lowered for adjustment, and the artery side liquid level adjusting means adjusts the liquid level in the artery side chamber when the pump is reversed.

The artery side chamber provided in the artery side circuit allows removal of air bubbles in the blood distributed through the artery side circuit. Furthermore, when the pump is reversed, the artery side liquid level adjusting means provided in the artery side circuit raises the liquid level in the artery side chamber to allow more reliable prevention of possible mixture of air into the blood.

Preferably, in the blood purifying device, the blood circuit includes a chamber allowing removal of air bubbles in the blood, and the chamber is allowed to be arranged upside down.

When the blood circuit includes the chamber allowed to be arranged upside down, the chamber may be arranged upside down with respect to an arrangement used during hemodialysis to enable blood to be extruded through a bottom portion of the chamber and circulated through the blood circuit when the pump is reversed. This enables possible mixture of air into the blood to be more reliably prevented without the liquid level adjusting means.

Furthermore, the present invention provides an access flow rate measuring method for measuring an access flow rate (X) of an access vessel, the access flow rate measuring method including a preparing step of preparing a blood purifying device including a dialysis unit bringing blood into contact with a dialysate, a blood circuit having an artery side circuit having an end connected to the dialysis unit and another end communicating with an upstream side of the access vessel of a patient and a vein side circuit having an end connected to the dialysis unit and another end communicating with a downstream side of the access vessel of the patient, the blood circuit distributing the blood, a pump capable of rotating in forward and reverse and provided in the artery side circuit to circulate the blood, and a measuring means provided in the vein side circuit to measure a blood indicator for the blood, the artery side circuit, the vein side circuit, and the dialysis unit being filled with a priming solution, a dialysate removing step of removing the dialysate from the dialysis unit to distribute, through the vein side circuit, the blood flowing through the access vessel of the patient, a first measuring step of using the measuring means in the dialysate removing step to measure an initial blood indicator for the blood distributed through the blood circuit and flowing through the access vessel of the patient, a diluting step of reversing the pump to cause the priming solution to flow out from the artery side circuit to dilute, with the priming solution, the blood distributed through the vein side circuit and flowing through the access vessel of the patient, and a second measuring step of using the measuring means to measure the blood indicator for the blood diluted with the priming solution.

The access flow rate measuring method according to the present invention uses the blood purifying device including the pump capable of rotating in forward and reverse. Forward rotation of the pump thus causes the blood to be distributed through the blood circuit and dialyzed in the dialysis unit, enabling the blood to be purified. Furthermore, when the pump is reversed to cause the priming solution to flow out from the artery side circuit, the blood diluted with the priming solution can be circulated. This allows the blood indicator for the blood diluted with the priming solution to be measured using the measuring means. Furthermore, as described above, the first measuring step includes measuring the blood indicator for the blood before being diluted with the priming solution (blood flowing through the access vessel of the patient), and the second measuring step includes measuring the blood indicator for blood after being diluted with the priming solution. This allows the access flow rate to be accurately measured. Moreover, a device similar to the device used for hemodialysis may be used in measuring the access flow rate. This eliminates a need for much time and effort during the measurement, allowing the access flow rate to be easily measured.

Preferably, the first measuring step includes measuring an initial blood indicator BC1 for the blood distributed through the blood circuit and flowing through the access vessel of the patient when the dialysate is removed in a state where the pump is stopped, and the second measuring step includes using the blood purifying device including the artery side circuit, the vein side circuit, and the dialysis unit all of which are filled with the priming solution, assuming that a flow rate of priming solution to flow out from the artery side circuit when the pump is reversed is S in the diluting step, measuring a blood indicator BC2 for blood diluted with the priming solution when the blood indicator for the blood diluted with the priming solution reaches a plateau, and calculating, based on Equation (1), the access flow rate (X) assuming that the access flow rate in the access vessel is not varied by the priming solution having flowed in from the artery side circuit.

$$X = BC2 \times S/(BC1 - BC2) \quad (1)$$

The access flow rate measuring method thus includes calculating the access flow rate based on the flow rate distributed through the measuring means when the pump is reversed and the blood indicator for the blood obtained before and after the dilution with the priming solution. This allows the access flow rate to be accurately and easily measured.

Preferably, in the access flow rate measuring method, the preparing step includes preparing the blood purifying device including a vein side chamber that allows removal of air bubbles in the blood and a vein side liquid level adjusting means for allowing a liquid level in the vein side chamber to be optionally raised and lowered for adjustment, and the vein side liquid level adjusting means adjusts the liquid level in the vein side chamber when a fluid flowing through the vein side circuit is refluxed.

The vein side chamber provided in the vein side circuit allows removal of air bubbles in the blood distributed through the vein side circuit. Furthermore, when the fluid flowing through the vein side circuit is refluxed, the vein side liquid level adjusting means provided in the vein side circuit raises the liquid level in the vein side chamber to allow more reliable prevention of possible mixture of air into the blood.

Preferably, in the access flow rate measuring method, the preparing step includes preparing the blood purifying device including an artery side chamber that allows removal of air bubbles in the blood and an artery side liquid level adjusting means for allowing a liquid level in the artery side chamber to be optionally raised and lowered for adjustment, and the artery side liquid level adjusting means adjusts the liquid level in the artery side chamber when the pump is reversed.

The artery side chamber provided in the artery side circuit allows removal of air bubbles in the blood distributed through the artery side circuit. Furthermore, when the pump is reversed, the artery side liquid level adjusting means provided in the artery side circuit raises the liquid level in the artery side chamber to allow more reliable prevention of possible mixture of air into the blood.

Preferably, in the access flow rate measuring method, the preparing step includes preparing the blood purifying device including a blood circuit provided with a chamber allowing removal of air bubbles in the blood, and arranging the chamber upside down.

When the blood circuit includes such a chamber, the chamber may be arranged upside down with respect to an arrangement used during hemodialysis and measure an access flow rate to enable blood to be extruded through a bottom portion of the chamber and circulated through the blood circuit when the pump is reversed. This enables possible mixture of air into the blood to be more reliably prevented without liquid level adjustment in the chamber by the liquid level adjusting means.

Preferably, the access flow rate measuring method includes causing the blood to flow from inside of a living organism into the blood circuit, and after the second measuring step, returning the blood diluted with the priming solution to the living organism.

As described above, the access flow rate measuring method according to the present invention includes diluting the blood with the priming solution for the access flow rate measurement, leading to a significant variation in the concentration of the blood. The access flow rate measuring method according to the present invention therefore enables accurate measurement of the access flow rate of the blood flowing through the living organism.

Advantageous Effects of Invention

The blood purifying device and the access flow rate measuring method according to the present invention allow the access flow rate of the access vessel to be accurately measured. Furthermore, the access flow rate can be easily measured without a need for much time and effort during the measurement.

DESCRIPTION OF EMBODIMENTS

An embodiment of a blood purifying device and an access flow rate measuring method according to the present invention will be described with reference to the drawings.

<Blood Purifying Device>

Figure 1:
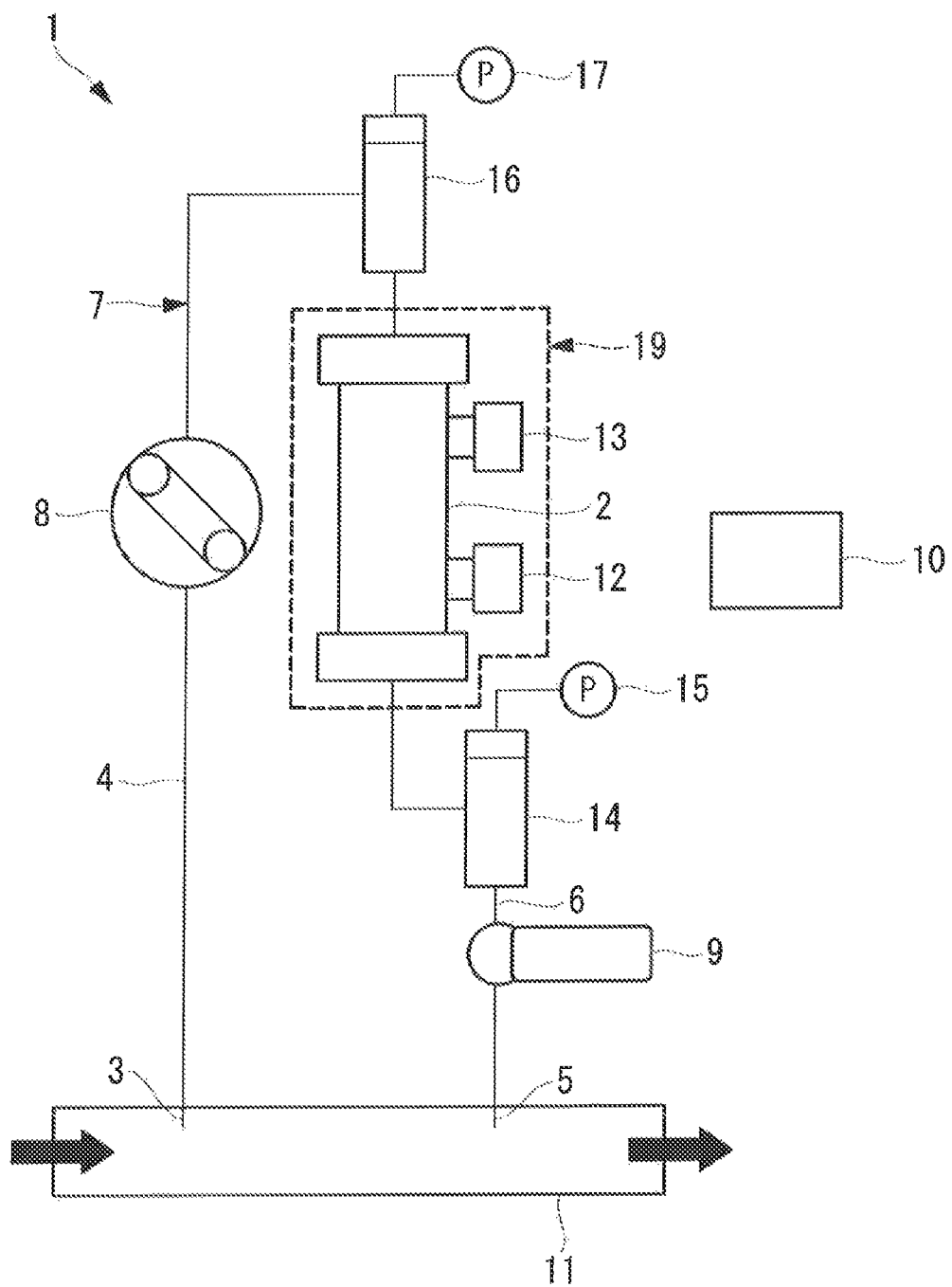
FIG. 1 is a schematic diagram illustrating an example of a blood purifying device according to the present invention.

FIG. 1 is a schematic diagram illustrating an example of a blood purifying device according to the present invention.

As illustrated in FIG. 1, a blood purifying device 1 according to the present invention includes a dialysis unit 2 bringing blood into contact with a dialysate, and a blood circuit 7 having an artery side circuit 4 having an end connected to the dialysis unit 2 and another end to which an artery side puncture needle 3 puncturing an upstream side of an access vessel 11 of a patient is connected and a vein side circuit 6 having an end connected to the dialysis unit 2 and another end to which a vein side puncture needle 5 puncturing a downstream side of the access vessel (shunt) 11 of the patient is connected, the blood circuit 7 distributing the blood.

The dialysis unit 2 has a semipermeable membrane or the like and is connected, via a dialysate inlet 12 and a dialysate outlet 13, to a dialysate line not illustrated in the drawings. During hemodialysis, the dialysis unit 2 brings blood distributed through the blood circuit 7 into contact with a dialysate. In this case, in the dialysis unit 2, a fresh dialysate is fed to the dialysis unit 2 through the dialysate line via the dialysate inlet 12. A used dialysate is discharged from the dialysis unit 2 to the dialysate line via the dialysate outlet 13.

Here, the artery side circuit 4 is provided with a pump 8 capable of rotating in forward and reverse and circulating the blood, the vein side circuit 6 is provided with a measuring means 9 for measuring a blood indicator for the blood. When the pump 8 is reversed to cause a priming solution to flow out from the artery side circuit 4, the blood flowing through the access vessel 11 can be diluted with the priming solution, and the blood diluted with the priming solution can be circulated through the blood circuit 7. The blood purifying device 1 is thus capable of measuring the blood indicator for the blood diluted with the priming solution using the measuring means 9. Furthermore, at the time of hemodialysis, the pump 8 is rotated forward to distribute the blood through the access vessel 11 to the blood circuit 7 via the artery side puncture needle 3. The distributed blood is then dialyzed in the dialysis unit 2 and can thus be purified.

The measuring means 9 measures the blood indicator for blood concentration or the like (for example, hemoglobin concentration, hematocrit, urea, or albumin). The principle of the measurement is as follows. For example, blood is irradiated with near infrared light emitted from a light emitting unit. A light receiving unit receives transmitted light transmitted through the blood. The concentration of the blood or the like can then be determined from a difference in the amount of near infrared light between the light emitting unit and the light receiving unit. To measure the access flow rate, the measuring means 9 is used to measure the blood indicator for the blood and to measure the access flow rate based on the result of the measurement.

Here, the measuring means 9 is preferably capable of measuring the hemoglobin concentration or the hematocrit in the blood. If the measuring means 9 is capable of measuring the hemoglobin concentration or the hematocrit in the blood, the measuring means 9 can measure the access flow rate based on the hemoglobin concentration or hematocrit in the blood. Furthermore, when the hemoglobin concentration or the hematocrit in the blood is measured before and after the dilution with the priming solution, the access flow rate can be more accurately measured.

First, with the pump 8 stopped, dialysate is removed through the dialysate outlet 13 to set the inside of the vein side circuit 6 to a negative pressure (system 19 removing the dialysate). An automatic blood removal function based on the above-described mechanism is used to remove blood through the vein side puncture needle 5 to distribute the blood through the vein side circuit 6 of the blood circuit 7. This allows the initial blood indicator for the blood distributed through the vein side circuit 6 and flowing through the access vessel 11 of the patient (that is, the blood indicator for the blood flowing through the patient's body) to be measured using the measuring means 9. The initial blood indicator may be measured by reversing the pump 8. However, in that case, dilution with the priming solution may affect the measurement, leading to a measurement error. The dialysate is therefore preferably removed with the pump stopped.

Then, to measure the access flow rate, the blood circuit 7 is filled with the priming solution and the pump 8 is reversed to inject the priming solution through the artery side puncture needle 3, while the blood is simultaneously removed from the access vessel 11 via the vein side puncture needle 5 and distributed through the vein side circuit 6. Here, the priming solution may be saline (aqueous solution containing approximately 0.9 wt % sodium chloride) or dialysate. However, the priming solution is not limited to these.

After the initial blood indicator for the blood is measured, the pump 8 is reversed to inject the priming solution through the artery side puncture needle 3 to dilute the blood flowing through the access vessel 11. The diluted blood flows in through the vein side puncture needle 5 and is distributed through the vein side circuit 6. This allows the blood indicator for the blood diluted with the priming solution to be measured using the measuring means 9.

Here, the blood purifying device 1 includes a flow rate calculating unit 10 calculating the access flow rate of the access vessel 11 based on the initial blood indicator obtained by the dialysate removal, the flow rate of the priming solution flowing out through the artery side puncture needle 3 when the pump 8 is reversed to cause the priming solution to flow out from the artery side circuit 4, and the blood indicator for the blood diluted with the priming solution. The flow rate calculating unit 10 allows the blood purifying device 1 to accurately measure the access flow rate of the access vessel 11 based on the flow rate obtained when the pump is reversed and the result of measurement of the blood indicator for the blood obtained before and after dilution with the priming solution.

The flow rate calculating unit 10 also preferably calculates the access flow rate (X) of the access vessel 11 based on Equation (1), based on the initial blood indicator BC1 for the blood distributed through the vein side circuit 6 and flowing through the access vessel 11 of the patient, the flow rate S distributed through the measuring means 9 when the pump 8 is reversed to cause the priming solution to flow out from the artery side circuit 4, and the blood indicator BC2 of the blood diluted with the priming solution which is obtained when the pump 8 is reversed to dilute, with the priming solution, the blood distributed through the vein side circuit 6 and flowing through the access vessel 11 of the patient.

$$X = BC2 \times S/(BC1-BC2) \quad (1)$$

The blood purifying device 1 thus calculates the access flow rate using Equation (1) based on the flow rate distributed through the measuring means 9 when the pump 8 is reversed and the blood indicator for the blood obtained before and after the dilution with the priming solution. This allows the access flow rate to be accurately and easily measured.

Preferably, the vein side circuit 6 includes a vein side chamber 14 that allows removal of air bubbles in the blood and a vein side liquid level adjusting means 15 for allowing a liquid level in the vein side chamber 14 to be optionally raised and lowered for adjustment, and the vein side liquid level adjusting means 15 adjusts the liquid level in the vein side chamber 14 when a fluid flowing through the vein side circuit 6 is refluxed. The vein side chamber 14 provided in the vein side circuit 6 allows removal of air bubbles in the blood distributed through the vein side circuit 6. Furthermore, when the fluid flowing through the vein side circuit 6 is refluxed, the vein side liquid level adjusting means 15 provided in the vein side circuit 6 raises the liquid level in the vein side chamber 14 to allow more reliable prevention of possible mixture of air into the blood.

Furthermore, the artery side circuit 4 includes an artery side chamber 16 that allows removal of air bubbles in the blood and an artery side liquid level adjusting means 17 for allowing a liquid level in the artery side chamber 16 to be optionally raised and lowered for adjustment, and the artery side liquid level adjusting means 17 adjusts the liquid level in the artery side chamber 16 when the pump 8 is reversed. The artery side chamber 16 provided in the artery side circuit 4 allows removal of air bubbles in the blood distributed through the artery side circuit 4. Furthermore, when the pump 8 is reversed, the artery side liquid level adjusting means 17 provided in the artery side circuit 4 raises the liquid level in the artery side chamber 16 to allow more reliable prevention of possible mixture of air into the blood.

The vein side liquid level adjusting means 15 and the artery side liquid level adjusting means 17 may be, although not limited to, for example, air pumps.

In the description of the present embodiment, by way of example, the blood purifying device 1 includes the vein side liquid level adjusting means 15 and the artery side liquid level adjusting means 17. However, these liquid level adjusting means may be omitted from the blood purifying device 1. Furthermore, the vein side chamber 14 and the artery side chamber 16 need also not necessarily be provided. Only one of the chambers may be provided, or neither of them may be provided. Of course, chambers similar to the chambers used during hemodialysis may be used as the vein side chamber 14 and the artery side chamber 16 to measure the access flow rate. To more reliably prevent possible mixture of air into the blood during reversal of the pump 8, the chambers used are most preferably provided with a blood inlet and a blood outlet at a bottom portion thereof if the above-described liquid level adjusting means are not provided. The chambers that may be arranged upside down may be used. When the blood circuit 7 includes a chamber that may be arranged upside down, the chamber may be arranged upside down with respect to an arrangement used during hemodialysis to enable blood to be extruded through a bottom portion of the chamber and circulated through the blood circuit 7 when the pump 8 is reversed. This enables possible mixture of air into the blood to be more reliably prevented without the liquid level adjusting means.

As described above, the blood purifying device according to the present embodiment is capable of accurately measuring the access flow rate. The blood purifying device according to the present embodiment is similar to the device used during hemodialysis and thus eliminates a need for much time and effort for measurement, allowing the access flow rate to be easily measured.

<Access Flow Rate Measuring Method>

Now, an example of an access flow rate measuring method according to the present invention will be described below.

The access flow rate measuring method according to the present invention includes a preparing step of preparing a blood purifying device including a dialysis unit bringing blood into contact with a dialysate, a blood circuit having an artery side circuit having an end connected to the dialysis unit and another end communicating with an upstream side of an access vessel of a patient and a vein side circuit having an end connected to the dialysis unit and another end communicating with a downstream side of the access vessel of the patient, the blood circuit distributing the blood, a pump capable of rotating in forward and reverse and provided in the artery side circuit to circulate the blood, and a measuring means provided in the vein side circuit to measure a blood indicator for the blood, the artery side circuit, the vein side circuit, and the dialysis unit being filled with a priming solution, a dialysate removing step of removing the dialysate from the dialysis unit to distribute, through the vein side circuit, the blood flowing through the access vessel of the patient, a first measuring step of using the measuring means in the dialysate removing step to measure an initial blood indicator for the blood distributed through the blood circuit and flowing through the access vessel of the patient, a diluting step of reversing the pump to cause the priming solution to flow out from the artery side circuit to dilute, with the priming solution, the blood distributed through the vein side circuit and flowing through the access vessel of the patient, and a second measuring step of using the measuring means to measure the blood indicator for the blood diluted with the priming solution.

(Preparing Step)

The preparing step includes preparing the blood purifying device including the above-described dialysis unit, blood circuit, pump, and measuring means. In the following description, by way of example, the blood purifying device 1 illustrated in FIG. 1 is prepared, and the following steps are executed. The artery side circuit 4, the vein side circuit 6, and the dialysis unit 2 are pre-filled with the priming solution.

In the preparing step, the blood purifying device 1 prepared preferably includes a vein side chamber 14, a vein side liquid level adjusting means 15, an artery side chamber 16, and an artery side liquid level adjusting means 17 as illustrated in FIG. 1. The vein side chamber 14 and artery side chamber 16 provided in the blood purifying device 1 allow removal of air bubbles in blood distributed through the vein side circuit 6 and the artery side circuit 4. Furthermore, the vein side liquid level adjusting means 15 and artery side liquid level adjusting means 17 provided in the blood purifying device 1 respectively raise liquid levels in the vein side chamber 14 and the artery side chamber 16, allowing more reliable prevention of possible mixture of air into the blood.

Additionally, the blood purifying device prepared is not limited to the blood purifying device 1 as illustrated in FIG. 1 but may lack the above-described liquid level adjusting means and chambers. Moreover, the blood circuit 7 of the blood purifying device prepared may include a chamber that allows removal of air in the blood, and the chamber may be arranged upside down when the access flow rate is measured. When the blood circuit 7 includes such a chamber, the access flow rate may be measured with the chamber arranged upside down with respect to the arrangement used during hemodialysis to allow the blood to be extruded through the bottom portion of the chamber and circulated through the blood circuit 7 when the pump 8 is reversed. This enables possible mixture of air into the blood to be more reliably prevented without liquid level adjustment in the chamber by the liquid level adjusting means.

(Dialysate Removing Step)

Figure 2:
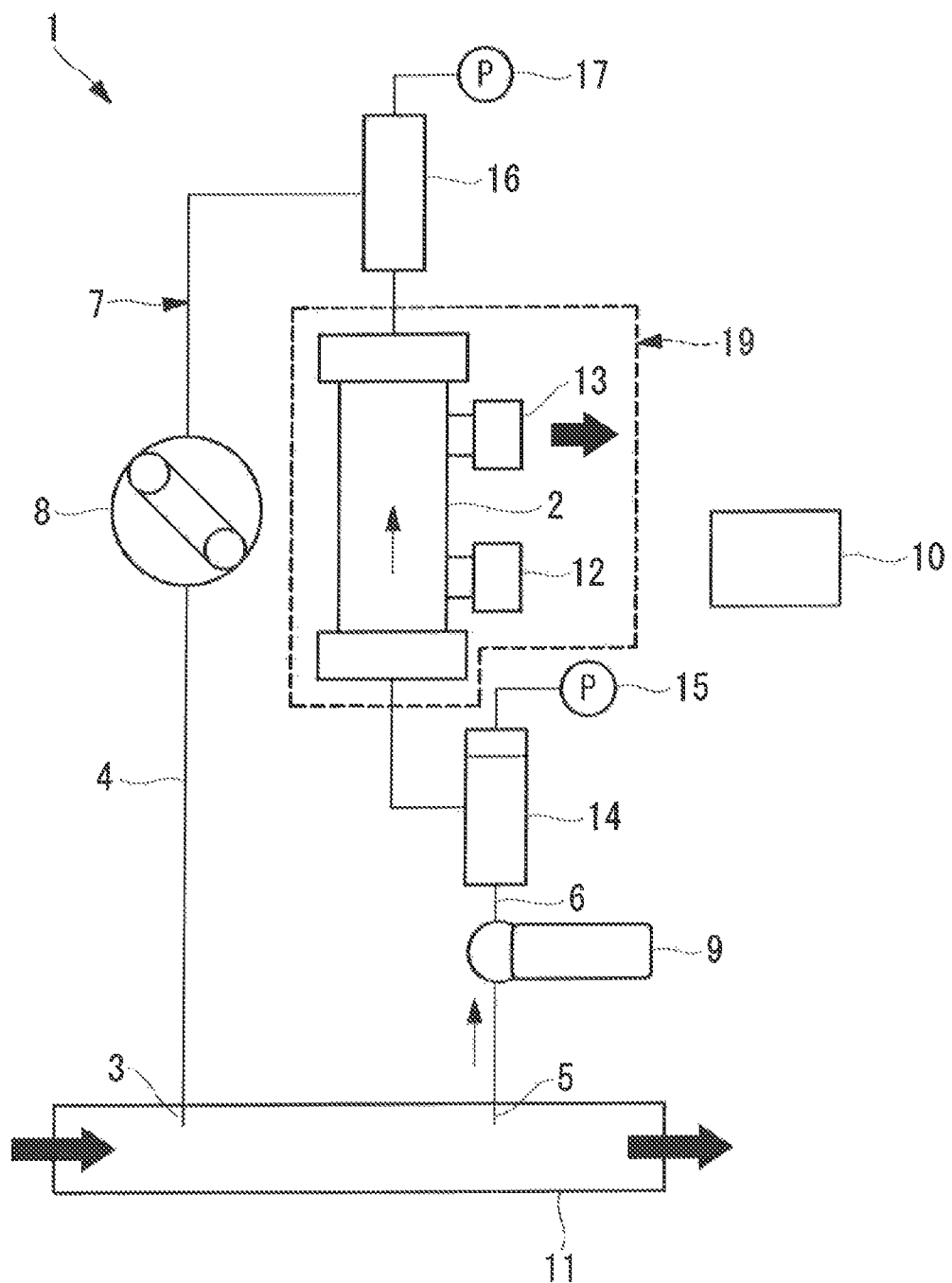
FIG. 2 is a schematic diagram illustrating a state where a dialysate removing step has been executed in the blood purifying device illustrated in FIG. 1.

The dialysate removing step includes stopping the pump 8 and using the system 19 removing the dialysate to remove the dialysate through the dialysate outlet 13 to set the inside of the vein side circuit 6 and blood circuit 7 to a negative pressure as illustrated in FIG. 2. The blood is thus removed from the access vessel 11 via the vein side puncture needle 5 to distribute, through the vein side circuit 6, the blood flowing through the access vessel 11 of the patient.

(First Measuring Step)

The first measuring step includes using the measuring means 9 to measure the initial blood indicator (BC1) for the blood distributed through the blood circuit 7 in the dialysate removing step and flowing through the access vessel 11 of the patient.

(Diluting Step)

Figure 3:
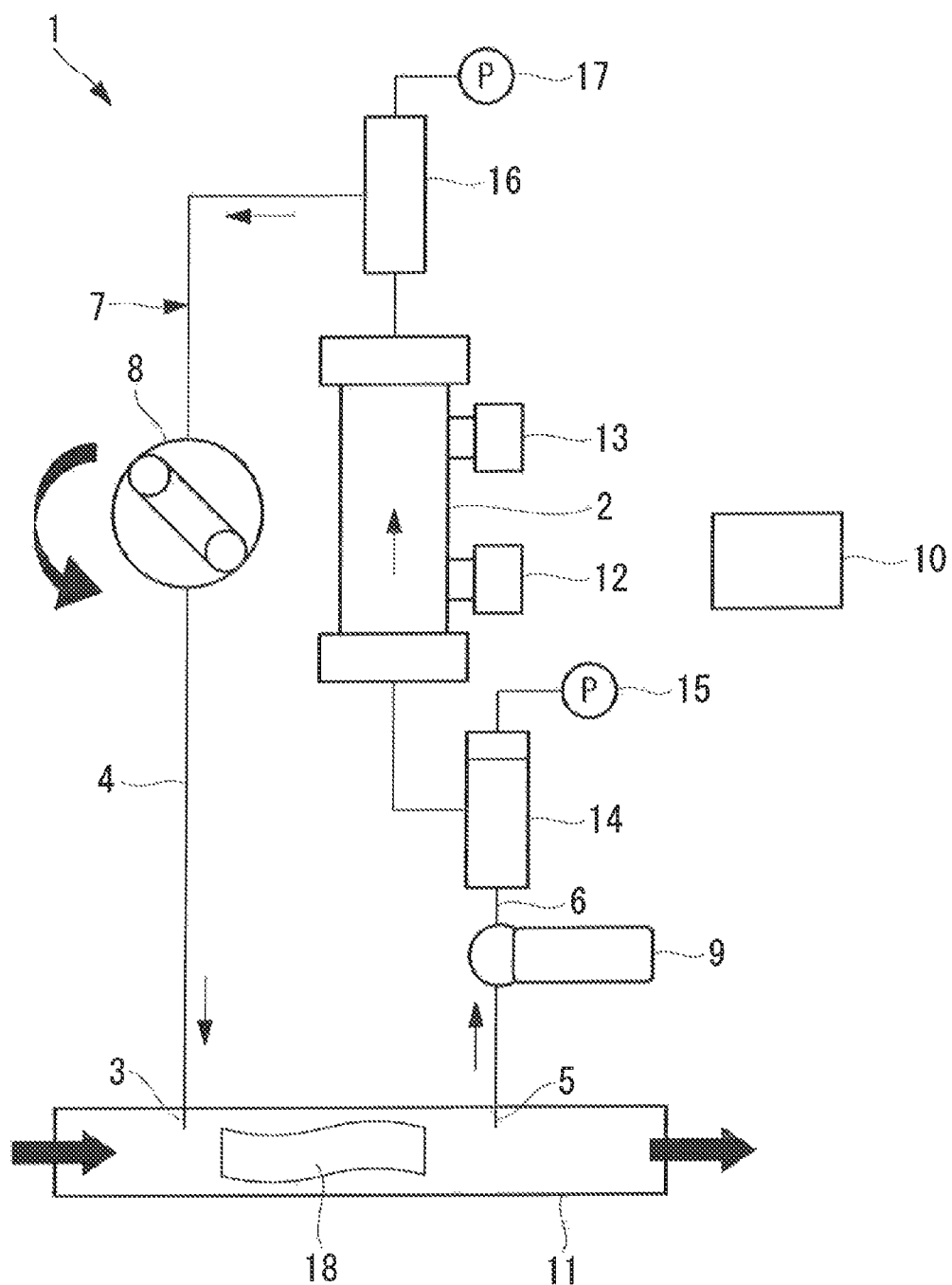
FIG. 3 is a schematic diagram illustrating a state where a diluting step has been executed in the blood purifying device illustrated in FIG. 1.

The diluting step is then executed. The diluting step includes stopping the dialysate removal and reversing the pump 8 to distribute, through the access vessel 11, the priming solution in the blood circuit 7 to dilute the blood in the access vessel 11 with the priming solution (preparation of the blood 18 diluted with the priming solution) as illustrated in FIG. 3. This causes the blood diluted with the priming solution to be distributed through the vein side circuit 6.

(Second Measuring Step)

In the second measuring step, the blood 18 diluted with the priming solution in the diluting step is distributed through the measuring means 9 via the vein side puncture needle 5. The blood indicator for the blood 18 is measured using the measuring means 9. Specifically, the blood is diluted in the diluting step, and the blood indicator (BC2) for the blood diluted with the priming solution is measured using the measuring means 9 when the blood indicator reaches a plateau. Once the BC2 measurement ends, the blood pump may immediately be rotated forward to shift to a hemodialysis step.

Figure 4:
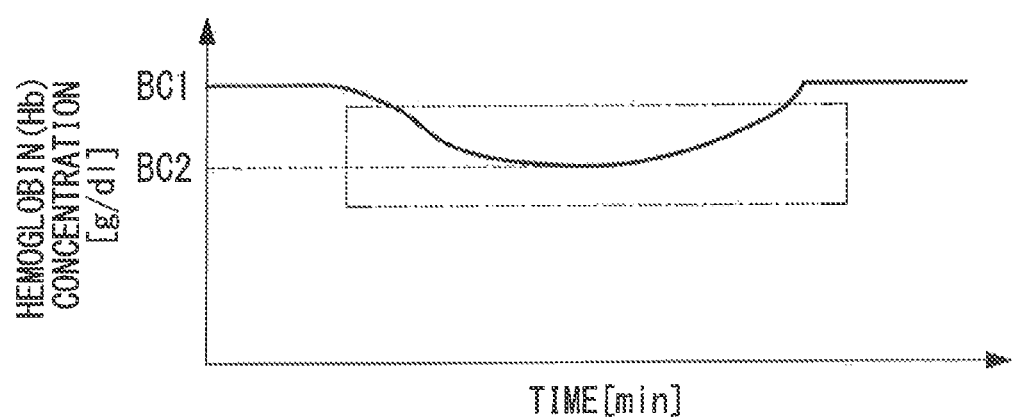
FIG. 4 is a graph illustrating a state where a blood indicator (hemoglobin concentration) for blood varies after the diluting step.

Now, a specific measuring method for the BC2 will be described in further detail with reference to FIG. 4 taking, as an example, a case where the blood indicator is the hemoglobin concentration in the blood. FIG. 4 is a graph illustrating a state where the hemoglobin concentration in the blood varies after the diluting step. The ordinate axis indicates the hemoglobin (Hb) concentration, and the abscissa axis indicates time. A left end (0 min) of the graph indicates the hemoglobin concentration in the blood that has not been diluted with saline (priming solution) yet. That is, the hemoglobin concentration at 0 min corresponds to the BC1.

The blood in the access vessel is then diluted with the saline, and the measured hemoglobin concentration decreases as illustrated in a part of FIG. 4 enclosed by an alternate long and short dash line. When a given time has elapsed since the start of the dilution, the hemoglobin concentration reaches a plateau. The hemoglobin concentration having reached the plateau corresponds to the BC2. After reaching the plateau, the liquid with which the circuit has been filled is replaced with blood, which is thus no longer diluted, with the hemoglobin concentration gradually increasing.

If the hemoglobin concentration in the blood is measured to measure the access flow rate of the access vessel, it is assumed that a flow rate transferred by the pump 8 and flowing out from the artery side puncture needle 3 when the pump 8 is reversed is S [ml/min] in the diluting step, and the hemoglobin concentration (BC1 and BC2) in the blood before and after the dilution with saline is measured in the first measuring step and the second measuring step. When it is assumed that the flow rate of the blood in the access vessel 11 is not varied by saline having flowed in through the blood circuit 7, since the amount of hemoglobin in the blood remains unchanged, a relationship in Equation (1) holds true. That is, the access flow rate (X [ml/min]) may be calculated based on Equation (1).

$$X = BC2 \times S/(BC1 - BC2) \quad (1)$$

Specifically, if $BC1=10$ g/dl, $BC2=8$ g/dl, and $S=200$ ml/min, $X=8\times200/(10-8)=800$ ml/min may be calculated based on Equation (1).

In the dialysis removing step in the access flow rate measuring method, the blood may be caused to flow from the inside of the living organism into the blood circuit 7 to allow acquisition of an accurate previous value not affected by the effect of dilution. Furthermore, in the second measuring step, based on the accurate BC1, the blood diluted with the priming solution is injected into the living organism, and the access blood flow is measured. In the access flow rate measuring method according to the present embodiment, the blood is diluted with the priming solution to measure the access flow rate. Thus, in the access flow rate measuring method according to the present embodiment, the indicator for the blood concentration varies much more significantly than in the current method executed after filling with blood. The access flow rate measuring method according to the present embodiment therefore enables accurate measurement of the flow rate of the blood flowing through the living organism.

As described above, the access flow rate measuring method according to the present embodiment allows accurate measurement of the access flow rate of the access vessel. Moreover, a device similar to the device used for hemodialysis may be used in measuring the access flow rate. This eliminates a need for much time and effort during the measurement, allowing the access flow rate to be easily measured.

REFERENCE SIGNS LIST

1 Blood purifying device
2 Dialysis unit
3 Artery side puncture needle
4 Artery side circuit
5 Vein side puncture needle
6 Vein side circuit
7 Blood circuit
8 Pump
9 Measuring means
10 Flow rate calculating unit
11 Access vessel
12 Dialysate inlet
13 Dialysate outlet
14 Vein side chamber
15 Vein side liquid level adjusting means
16 Artery side chamber
17 Artery side liquid level adjusting means
18 Blood diluted with priming solution
19 System removing dialysate

The invention claimed is:

1. A blood purifying method using a blood purifying device, the method comprising:
bringing, using a dialysis unit, blood into contact with a dialysate; and
calculating an access flow rate of an access vessel of a patient, wherein
the blood purifying device includes
the dialysis unit,
a blood circuit having
an artery side circuit having an end connected to the dialysis unit and another end to which an artery side puncture needle is connected, the artery side puncture needle being configured to puncture an upstream side of the access vessel, and a vein side circuit having an end connected to the dialysis unit and another end to which a vein side puncture needle is connected, the vein side puncture needle being configured to puncture a downstream side of the access vessel of the patient, the blood circuit distributing the blood, the artery side circuit is provided with a pump configured to rotate in forward and reverse and circulate the blood, and the calculating calculates the access flow rate based on (1) an initial blood indicator, the initial blood indicator being a blood indicator for blood distributed through the vein side circuit and flowing through the access vessel of the patient, the initial blood indicator being obtained by removing the dialysate from the dialysis unit without relying on the pump, (2) a flow rate distributed through the vein side circuit when the pump is reversed to cause a priming solution to flow out from the artery side circuit, and (3) a diluted blood indicator, the diluted blood indicator being the blood indicator for blood diluted with the priming solution when the pump is reversed to dilute, with the priming solution, the blood distributed through the vein side circuit and flowing through the access vessel of the patient.

2. The blood purifying method according to claim 1, wherein
the blood indicator for blood is a hemoglobin concentration or hematocrit in the blood.

3. The blood purifying method according to claim 1, wherein
based on:
the initial blood indicator (BC1) for the blood distributed through the vein side circuit and flowing through the access vessel of the patient,
a flow rate (S) distributed through the vein side circuit when the pump is reversed to cause the priming solution to flow out from the artery side circuit, and
the diluted blood indicator (BC2) for the blood diluted with the priming solution which is obtained when the pump is reversed to dilute, with the priming solution, the blood distributed through the vein side circuit and flowing through the access vessel of the patient,
the access flow rate (X) of the access vessel is calculated based on a following Equation (1):

$$X = BC2 \times S/(BC1 - BC2) \qquad (1)$$

4. The blood purifying method according to claim 1, wherein
the vein side circuit includes a vein side chamber that allows removal of air bubbles in the blood and a vein side liquid level adjusting pump that allows a liquid level in the vein side chamber to be optionally raised and lowered for adjustment, and the vein side liquid level adjusting pump adjusts the liquid level in the vein side chamber when a fluid flowing through the vein side circuit is refluxed.

5. The blood purifying device method according to claim 1, wherein
the artery side circuit includes an artery side chamber that allows removal of air bubbles in the blood and an artery side liquid level adjusting pump that allows a liquid level in the artery side chamber to be optionally raised and lowered for adjustment, and the artery side liquid level adjusting pump adjusts the liquid level in the artery side chamber when the pump is reversed.

6. The blood purifying method according to claim 1, wherein
the blood circuit includes a chamber allowing removal of air bubbles in the blood, and the chamber is arranged upside down with respect to an arrangement of the chamber used during hemodialysis.

7. An access flow rate measuring method for measuring an access flow rate (X) of an access vessel, the access flow rate measuring method comprising:
preparing a blood purifying device, the blood purifying device including
a dialysis unit bringing blood into contact with a dialysate, and
a blood circuit having
an artery side circuit having an end connected to the dialysis unit and another end communicating with an upstream side of the access vessel of a patient, and
a vein side circuit having an end connected to the dialysis unit and another end communicating with a downstream side of the access vessel of the patient, the blood circuit distributing the blood, and
a pump capable of rotating in forward and reverse and provided in the artery side circuit to circulate the blood,
the artery side circuit, the vein side circuit, and the dialysis unit being filled with a priming solution;
removing the dialysate from the dialysis unit to distribute, through the vein side circuit, blood flowing through the access vessel of the patient;
while removing the dialysate from the dialysis unit, measuring an initial blood indicator, the initial blood indicator being a blood indicator for blood distributed through the blood circuit and flowing through the access vessel of the patient;
reversing the pump to cause the priming solution to flow out from the artery side circuit to dilute, with the priming solution, the blood distributed through the vein side circuit and flowing through the access vessel of the patient; and
measuring a diluted blood indicator, the diluted blood indicator being the blood indicator for blood diluted with the priming solution.

8. The access flow rate measuring method according to claim 7, wherein
based on:
the initial blood indicator (BC1) for the blood distributed through the vein side circuit and flowing through the access vessel of the patient,
a flow rate (S) distributed through the vein side circuit when the pump is reversed to cause the priming solution to flow out from the artery side circuit, and
the diluted blood indicator (BC2) for the blood diluted with the priming solution which is obtained when the pump is reversed to dilute, with the priming solution, the blood distributed through the vein side circuit and flowing through the access vessel of the patient,
the access flow rate (X) is calculated using a following Equation (1):

$$X = BC2 \times S/(BC1 - BC2) \qquad (1)$$

9. The access flow rate measuring method according to claim 7, wherein
the preparing includes preparing the blood purifying device including the vein side circuit provided with a vein side chamber that allows removal of air bubbles in the blood and a vein side liquid level adjusting pump that allows a liquid level in the vein side chamber to be optionally raised and lowered for adjustment, and the vein side liquid level adjusting pump adjusts the liquid level in the vein side chamber when a fluid flowing through the vein side circuit is refluxed.

10. The access flow rate measuring method according to claim 7, wherein the preparing includes preparing the purifying device including the artery side circuit provided with an artery side chamber that allows removal of air bubbles in the blood and an artery side liquid level adjusting pump that allows a liquid level in the artery side chamber to be optionally raised and lowered for adjustment, and the artery side liquid level adjusting pump adjusts the liquid level in the artery side chamber when the pump is reversed.

11. The access flow rate measuring method according to claim 7, wherein the preparing includes preparing the blood purifying device including the blood circuit provided with a chamber allowing removal of air bubbles in the blood; and arranging the chamber upside down with respect to an arrangement of the chamber used during hemodialysis.

12. The access flow rate measuring method according to claim 7, wherein the removing includes causing the blood to flow from inside of a living organism into the blood circuit, and after measuring the diluted blood indicator, the blood diluted with the priming solution is returned to the living organism.

* * * * *